United States Patent [19]
Menzel et al.

[11] Patent Number: 5,993,857
[45] Date of Patent: Nov. 30, 1999

[54] COSMETIC SKIN CLEANSER BASED ON NATURAL ACTIVE SUBSTANCES

[75] Inventors: Anette Menzel, Morris Plains; Ralph Macchio, Flanders; Klaus Stanzl, White Plains, all of N.J.; Leonhard Zastrow, Monaco, Monaco

[73] Assignee: Lancaster Group GmbH, Mainz, Germany

[21] Appl. No.: 09/091,975

[22] PCT Filed: Jan. 17, 1997

[86] PCT No.: PCT/DE97/00117

§ 371 Date: Jun. 26, 1998

§ 102(e) Date: Jun. 26, 1998

[87] PCT Pub. No.: WO97/25974

PCT Pub. Date: Jul. 24, 1997

[51] Int. Cl.$^6$ ................................ A61K 7/00; A61K 9/14
[52] U.S. Cl. .................... 424/489; 424/450; 424/489; 424/490; 514/828; 514/844; 514/846; 514/847
[58] Field of Search ..................................... 424/401, 450, 424/489, 490, 491; 514/828, 844, 846, 847

[56] References Cited

U.S. PATENT DOCUMENTS 4,673,526  6/1987  Zabotto et al. .................... 252/174.16
5,215,759  6/1993  Mausner ................................. 424/489

FOREIGN PATENT DOCUMENTS

| 0486394B1 | 11/1991 | European Pat. Off. . |
| 0254447A | 1/1998 | European Pat. Off. . |
| 678488A5 | 9/1991 | Switzerland . |
| WO 93/13754 | 7/1993 | WIPO . |
| WO 94/12151 | 6/1994 | WIPO . |

OTHER PUBLICATIONS

JP 6–219924 A, IN: Patents Abstracts of Japan C–1271, Nov. 10, No. 588.

*Primary Examiner*—Thurman K. Page
*Assistant Examiner*—Sharon Howard
*Attorney, Agent, or Firm*—Collard & Roe, P.C.

[57] ABSTRACT

A cosmetic skin cleanser based on natural active ingredients is disclosed. The cleanser comprises an aqueous non-oily suspension of microspheres of a polyoxymethylene urea containing a natural liquid vegetable oil, and agents based on natural substances for moisturizing the skin. The agents could be aloe vera gel, jojoba oil, cetaryl glucosides, or a mixture of sarcosine, wheat amino acids and palmitic acid, and mixtures thereof, plus propylene glycol as an additional ingredient. The cleanser also includes one or more natural emulsifiers, natural cleansing substances and other excipients and vehicles.

14 Claims, No Drawings

COSMETIC SKIN CLEANSER BASED ON NATURAL ACTIVE SUBSTANCES

The invention relates to a cosmetic cleanser based on natural ingredients with an especially gentle and mild effect on the skin.

U.S. Pat. No. A 4,673,526 discloses an agent for deep cleansing of the skin, which is an anhydrous cleaning composition with an oily phase, an emulsifier and a particulate abrasive substance such as xanthan gum, carboxymethylamides, cellulose ethers, hydroxyalkylcelluloses or copolymers of acrylic acid and acrylamide.

W094/12151 discloses skin cleansers based on agglomerated silicon dioxide particles.

Swiss Patent CH-A 678,488 describes polyethylene microspheres as the base for a cleanser formulation.

The object of the present invention is to develop a skin cleanser that contains essentially natural cosmetic ingredients as the active ingredients and thus yields a mild but sufficiently intense skin cleaning effect.

This object is achieved according to this invention with a cosmetic skin cleanser based on essentially natural ingredients, comprising an aqueous non-oily suspension, containing (a) microspheres of a polyoxymethylene urea containing a natural liquid vegetable oil, (b) natural-based substances for moisturizing the skin, selected from aloe vera gel, jojoba oil, cetaryl glucoside, lipacids PVB and mixtures thereof, and propylene glycol as an additional substance, (c) one or more natural emulsifiers, (d) natural cleansing substances; and (e) other excipients and vehicles.

Lipacids PVB is a mixture of sarcosine, wheat amino acids and palmitic acid.

A preferred vegetable oil is jojoba oil, galam butter, avocado oil, avocadin, calendula oil and apricot kernel oil, in particular jojoba oil.

A preferred emulsifier is cetaryl glucoside, methyl glucose, sesquistearate and polyglycerol 3-methyl glucose distearate, in particular cetaryl glucoside. The emulsifier may be present in a concentration of approximately 1 to 7 percent by weight.

Cetaryl glucoside (CTFA name) is a valuable plant-based component whose ingredients are extraction products. For example, the glucose is extracted from corn and the fat from coconut oil. The glucolipid structure is free of chemical impurities and the usual solvents. It has both emulsifying and moisturizing effects.

Decyl polyglucose and acyl glutamate (CTFA terminology), the preferred cleansing substances, are surface-active agents which are also derived from natural substances. The detergent substance may be present in an amount of approximately 1 to 15 percent by weight, preferably 3–10 percent by weight.

The microspheres of polyoxymethylene urea used according to this invention have an average diameter of 160 to 200 $\mu$m, for example, and are in the form of a soft powder with a slightly granular texture. They are hollow on the inside and filled with the vegetable oil, they have a mild abrasive effect when rubbed on wet skin, and thus they thoroughly remove the dead cells from the skin. At the same time, the hollow spheres are opened when rubbed on the skin, so the oil they contain is released and can develop its moisturizing and soothing skin care effect.

Other active ingredients that may be present in the preparation according to this invention include dexpanthenol, hyaluronic acid, phospholipids and honey extract.

It has been found that due to the interaction of all the components of the formulation, not only does the desired cleansing effect occur, i.e., the dead skin cells are removed, but also a great improvement in the softness of the skin can be observed.

A surprising effect is that it has an extremely good moisturizing effect on the skin, which is more than 100% better than that of comparable preparations. The conventional cosmetic vehicles and excipients which should still be contained in the preparation according to this invention include emulsifiers, various oil components (such as fats, oils, esters, silicone oil, etc.), other ingredients such as allantoin, thickeners, preservatives, perfume oils, chelating agents, active ingredients such as allantoin, and water.

The skin cleanser preparation according to this invention is advantageously applied to wet skin and rubbed into the skin for a few minutes with a circular massaging action. Then it is rinsed off with warm water. When skin is cleansed in this way, an especially natural and uniform skin color is achieved when a self-tanning agent, for example, is applied subsequently. Such a combination of cleansing and tanning is therefore also within the scope of the present invention.

Irritation tests performed with a skin cleanser preparation according to this invention resulted in practically no irritation, thereby confirming the advantageously mild effect of the cosmetic preparation.

The invention is explained in greater detail below on the basis of examples, although they are not intended to restrict the scope of the invention in any way. The percentage amounts given are always based on weight, unless otherwise indicated. In some cases the CTFA terminology was used for the ingredients.

Example 1

| Phase A | |
|---|---|
| cetaryl glucoside | 5% |
| hexyl laurate | 7% |
| beeswax | 1% |
| isononyl isononate | 8% |
| wheat proteins | 0.3% |
| vitamin C + E mixture | 0.1% |
| Phase B | |
| deionized water | 42.1% |
| D gluconic acid | 5% |
| propylene glycol | 2% |
| triethanolamine | 0.2% |
| Phase C | |
| laureth-7/polyacrylamide/C13–14 isoparaffin | 4% |
| Phase D | |
| preservative | 0.8% |
| Phase E | |
| perfume | 0.5% |
| Phase F | |
| decyl polyglucose | 7% |
| Phase G | |
| deionized water | 1% |
| aloe vera gel | 1% |
| Phase H | |
| polyethylene | 11% |
| Phase I | |
| polyoxymethylene urea capsules (3M brand PMU capsules ®) with approx. 65% jojoba oil | 4% |

Eight phases were prepared separately and mixed together one after the other, homogenizing well. Phases A through D were incorporated at an elevated temperature (40° C. to 70°

C.), and finally phases E through I were incorporated at ambient temperature (less than 35° C.).

This yielded a mild, creamy emulsion with cleansing, smoothing and moisturizing properties. The cream was applied to damp skin and massaged in by rubbing in a circular movement. The mild (gentle) abrasives (peeling agents) removed dead skin cells and led to a uniformly soft appearance of the skin.

EXAMPLE 2

| Phase A | |
|---|---|
| cetaryl glucoside | 3% |
| hexyl laurate | 10% |
| beeswax | 3% |
| isononyl isononanote | 5% |
| wheat proteins | 0.2% |
| mixture of vitainin C + E | 0.2% |
| Phase B | |
| deionized water | 43.1% |
| D-gluconic acid | 3% |
| propylene glycol | 3% |
| triethanolamine | 0.2% |
| Phase C | |
| laureth-7/polyacrylamide/C13–14 isoparaffin | 4.5% |
| Phase D | |
| preservative | 0.8% |
| Phase E | |
| perfume | 0.5% |
| Phase F | |
| decyl polyglucose | 5% |
| Phase G | |
| deionized water | 1% |
| aloe vera gel | 1.5% |
| Phase H | |
| polyethylene | 11% |
| Phase I | |
| polyoxymethylene urea capsules with approx. 65% jojoba oil | 5% |

Eight phases were prepared separately, mixed together in succession and homogenized well. Phases A through D were incorporated at an elevated temperature (40° C. to 70° C.), and phases E through I were finally incorporated at ambient temperature (below 35° C.).

This yielded a cream with the same properties as in Example 1 above.

Comparative Example 1

The cream according to this invention as in Example 1 ("A" in the table) was subjected to a comparison test with a commercial product ("B" in the table, Oil of Olay) which also had a moisturizing and cleansing effect on the skin.

Two mg of the preparation was applied per cm² skin on an area of skin moistened previously, then washed off and dried.

The measurement was performed with an AFM Corneometer®.

Table 1 below shows the results of these measurements.

TABLE 1

| a) average | | Improvement in moisturizing effect | |
|---|---|---|---|
| b) scattering | | A | B |
| Before | a) | 0.9% | 0.3% |
| | b) | 1.8 | 2.4 |
| Immediately | a) | 31.9% | 23.9% |
| | b) | 5.8 | 6.5 |
| After 0.5 h | a) | 10.2% | 3.2% |
| | b) | 2.5 | 1.3 |
| After 1 h | a) | 7.8% | 4.2% |
| | b) | 2.6 | 1.9 |
| After 2 h | a) | 5.7% | 2.1% |
| | b) | 2.0 | 1.8 |
| After 3 h | a) | 3.0% | 1.3% |
| | b) | 2.0 | 1.7 |

We claim:

1. A cosmetic skin cleanser preparation based on natural active ingredients, comprising an aqueous non-oily suspension, comprising
   (a) microspheres of a polyoxymethylene urea containing a natural liquid vegetable oil,
   (b) agents based on natural substances for moisturizing the skin, selected from the group consisting of aloe vera gel, jojoba oil, cetaryl glucosides, a mixture of sarcosine, wheat amino acids and palmitic acid and mixtures thereof, and propylene glycol as an additional ingredient,
   (c) one or more natural emulsifiers,
   (d) natural cleansing substances, and
   (e) other excipients and vehicles.

2. A cosmetic skin cleanser preparation according to claim 1, wherein the natural vegetable oil is jojoba oil.

3. A cosmetic skin cleanser preparation according to claim 1, wherein the emulsifier is cetaryl glucoside.

4. A cosmetic skin cleanser preparation according to claim 1, wherein the natural cleansing substance is decyl polyglucose.

5. A cosmetic skin cleanser preparation according to claim 1, wherein the suspension contains proteins as nutrients for the skin.

6. A cosmetic skin cleanser preparation according to claim 1, wherein the suspension contains radical scavengers and/or antioxidants selected from the group consisting of vitamin C, E and mixtures thereof.

7. A cosmetic skin cleanser preparation according to claim 1, wherein the suspension contains emollients.

8. A cosmetic skin cleanser preparation according to claim 1, wherein the suspension contains microspheres in the amount of 0.5 to 10 percent by weight.

9. A cosmetic skin cleanser preparation according to claim 1, wherein the suspension contains the moisturizing agents in an amount of 9 to 15 percent by weight.

10. A cosmetic skin cleanser preparation according to claim 1, wherein the emulsifier content in the suspension is 1 to 7 percent by weight.

11. A cosmetic skin cleanser preparation according to claim 1, wherein the suspension contains the cleansing substances in an amount of 1 to 15 percent by weight.

12. A cosmetic skin cleanser preparation according to claim 5, wherein the proteins are wheat proteins.

13. A cosmetic skin cleanser preparation according to claim 8, wherein the amount of microspheres is in the range of 0.5 to 5 percent by weight.

14. A cosmetic skin cleanser preparation according to claim 9, wherein the amount of moisturizing agents is in the range of 9 to 11 percent by weight.

* * * * *

UNITED STATES PATENT AND TRADEMARK OFFICE
CERTIFICATE OF CORRECTION

PATENT NO. : 5,993,857
DATED : November 30, 1999
INVENTOR(S) : MENZEL ET AL

It is certified that error appears in the above-indentified patent and that said Letters Patent is hereby corrected as shown below:

On the title page, column 1, after Item [87], please insert

--[30]  Foreign Application Priority Data

Jan. 17, 1996  [DE]  Germany ............ 196 03 019.6--

Signed and Sealed this

Twenty-fifth Day of July, 2000

Attest:

Q. TODD DICKINSON

*Attesting Officer*  *Director of Patents and Trademarks*